United States Patent [19]
Bloom

[11] Patent Number: 4,964,848
[45] Date of Patent: Oct. 23, 1990

[54] TREATMENT OF MULTIPLE SCLEROSIS WITH LYMPHOCYTAPHERESIS AND CHEMO-IMMUNOSUPPRESSION

[76] Inventor: Philip M. Bloom, 12508 Briarwood Ter., Minnetonka, Minn. 55343

[21] Appl. No.: 212,209

[22] Filed: Jun. 27, 1988

[51] Int. Cl.$^5$ ............................................. A61M 37/00
[52] U.S. Cl. .......................................................... 604/6
[58] Field of Search ........................................ 604/4–6, 604/20; 128/897, 898; 514/903

[56] References Cited

U.S. PATENT DOCUMENTS

| | | | |
|---|---|---|---|
| 3,802,432 | 4/1974 | Djerassi | 128/214 |
| 3,892,236 | 7/1975 | Djerassi | 604/6 |
| 4,331,145 | 5/1982 | Winter | 604/20 |
| 4,362,155 | 12/1982 | Skerkovich | 128/214 |
| 4,428,744 | 1/1984 | Edelson | 604/6 |
| 4,521,405 | 6/1985 | McMichael | 424/92 |
| 4,614,513 | 9/1986 | Bensinger | 604/6 |
| 4,617,319 | 10/1986 | Kerwar | 514/647 |
| 4,673,385 | 6/1987 | Popovich et al. | 604/28 |
| 4,683,889 | 8/1987 | Edelson | 604/6 |
| 4,695,459 | 9/1987 | Steinman | 424/95 |
| 4,708,713 | 11/1987 | Lentz | 604/5 |

FOREIGN PATENT DOCUMENTS 0184040  6/1986  European Pat. Off. ............ 514/903

OTHER PUBLICATIONS

Meneghetti et al., "Lymphocytapheresis and Immunosuppressive Drugs in the Treatment of MS", 13th World Congress of Neurology, Hamburg, West Germany, Sept. 1–6, 1985, J. Neurol 232 (Suppl.) 1985, p. 125.
Ferla et al., "Effect of LCA Plus Cyclophosphamide on ... MS", et al. J. Neurol. Sci. 6:283–286, 1985.
Maida et al., "Long-Term LCA Therapy in MS", Eur. Neurol. 25:225–232 (1986).
Hauser et al., "LCA in Chronic Progressive MS", Neurology, vol. 34, pp. 922–926, Jul., 1984.
Knight, "The Effect of Intensive Immunosuppression on the In Vitro Activity of Lymphocytes from MS Patients", Post Graduate Medical J., 1976, vol. 52, Suppl. 5, pp. 131–134.
Paty et al., "Suppressor T Cells in MS: Do Changes in Numbers Vary with Clinical Activity?", Annals of the N.Y. Academy of Sciences, vol. 436, pp. 267–270, 1984.
Kurtzke, "Disability Rating Scales in Multiple Sclerosis", Annals of the N.Y. Academy of Sciences, *Multiple Sclerosis*, vol. 436, pp. 347–360, 1984.
Ellison et al., "Therapeutic Trials in Multiple Sclerosis: Azathioprine", Ann. of the N.Y. Academy of Sci., *Multiple Sclerosis, vol. 436, pp. 361–365, 1984.*
Khatri et al., "Plasmopherosis and Combined Immunosuppressive Drug Therapy in Chronic Progressive MS", Ann. of the N.Y. Acad. of Sci., *MS*, vol. 436, pp. 389–396, 1984.
Hafstein et al., "Total Lymphoid Irradiation in Chronic Progressive Multiple Sclerosis", Ann. of the N.Y. Academy of Sci, *MS*, vol. 436, pp. 397–409, 1984.
Devereux, Hafstein et al., "Effect of Total Lymphoid Radiation ... ", Neurology 38 (Suppl. 2) Jul., 1988, pg. 32, Same, Cook p. 41.
Silberberg, "Azathioprine in Multiple Sclerosis ... ", Neurology 38 (Suppl. 2), Jul., 1988, pp. 24–26.
British & Dutch MS-Group, "Double-Masked Trial of Azathioprine in MS", The Lancet, Jul. 23, 1988, pp. 179–183.
Intensive Immunosuppression in Progressive MS, New Eng. Jour. Med, vol. 308, No. 4, Jan. 27, 1983.
Plasma Exchange of Lymphocytapheresis in MS, Int. Jour. Artif. Organs, 7 pp. 39–42.
Long Term Lymphacytapheresis Therapy in MS, Eur. Neurol. 25, pp. 225–236.

*Primary Examiner*—C. Fred Rosenbaum
*Assistant Examiner*—Sharon Rose
*Attorney, Agent, or Firm*—James V. Harmon

[57] ABSTRACT

Autoimmune diseases, such as multiple sclerosis, are treated by conducting lymphocytapheresis in a series of treatments until the peripheral blood lymphocyte count has been reduced to less than 500 cells/$\mu$l and preferably to less than 300 cells/$\mu$l and thereafter continuing such treatments while administering an immunosuppressive compounds such as azathioprine at about 2.5 mg/Kg per day and prednisone at about 15 mg per day sufficient to maintain the PBL count at less than 500 cells/$\mu$l and preferably less than 300 cells/$\mu$l.

8 Claims, 1 Drawing Sheet

TREATMENT OF MULTIPLE SCLEROSIS WITH LYMPHOCYTAPHERESIS AND CHEMO-IMMUNOSUPPRESSION

FIELD OF THE INVENTION

The invention relates to treatment of autoimmune diseases and particularly multiple sclerosis. More specifically, the invention is concerned with the combined use of lymphocytapheresis (LCP) and chemotherapy.

BACKGROUND OF THE INVENTION

Multiple sclerosis is a disease of the central nervous system with variable neurologic deficits due to demyelination in the brain and spinal cord. The course of the disease is variable, in some patients multiple sclerosis is chronic and progressive. Although the etiology is not precisely understood, there is convincing evidence that the disease is of an autoimmune nature. Defective and abnormal immune responses have been observed. Current evidence indicates that the defective immune response causes destruction of central nervous system myelin by the autoreactive (cytotoxic lymphocyte) cells. The damage is initiated in two stages: In the first stage, T4 (helper-inducer) cells stimulate the T8 CTL cells to proliferate; and in the second stage, the T4 and the T8 cells are believed to be a direct cause of primary lesions. During this process the T4 cells recruit macrophages which may also cause direct cell damage. It is thus believed that the T4 cells mediate this autoimmune process. Finally, there is evidence that a basic defect in the T4 cell is a failure to induce proliferation of another subset of T8 suppressor cells which would normally inhibit the above progression. The defective T4 suppressor-inducer cells thus fail to perform the normal inhibitory function.

As a result of these immunological defects, attempts have been made to interrupt the course of the disease with immunosuppression. See: (1) "Intensive Immunosuppression in Progressive Multiple Sclerosis," New England Journal of Medicine, Vol. 308, No. 4, Jan. 1983, S. L. Hauser, et al; (2) "Plasma Exchange and Lymphocytapheresis in Multiple Sclerosis," Int J Artif Organs, 7:39–42, 1984, P. Hocker, et al; and (3) "Long-Term Lymphocytapheresis Therapy in Multiple Sclerosis," Eur Neurol, 25:225–236, 1986, E. Maida, et al.

In reference 1, 58 patients were divided into three groups. All patients received ACTH $R_x$ and one of the three groups received only ACTH. The second group received high-dose cyclophosphamide and the third group was treated with plasma exchange and low-dose cyclophosphamide administered orally. It was discovered that high-dose cyclophosphamide plus ACTH was the most effective in halting disease progression. However, in this study there was no lymphocytapheresis. Patients were treated with low-dose (2 mg/Kg/day unless the WBC was less than 4000 $\mu$l) intravenous cyclophosphamide and ACTH for producing hydrocortisone by stimulating the adrenal gland. In the plasmapheresis group, the cyclophosphomide was administered orally.

In reference 2, treatment with azathioprine and prednisone was combined with plasmapheresis, performed either four times in two weeks or two to three times in one week. In patients with persistent disease of over five years duration, there was an improvement in 50% to 70% of the cases. In this protocol there was no maintenance lymphocytapheresis, and the number of lymphocytes removed and the numbers of peripheral blood lymphocytes were not monitored.

In reference 3, a long-term therapy was administered without an intense induction phase. In this protocol, the number of lymphocytes removed was determined but the PBL counts were not monitored as the measure of effective therapy. Improvement was obtained in 3 of 9 patients, and a decrease in the relapse rate in 6 of 9 patients was observed. There were no relapses in 7 of 9 patients while on LCP. In this treatment lymphocytapheresis was not combined with any other therapy. Two-thirds of the patients remained unchanged but suffered exacerbations less often.

SUMMARY OF THE INVENTION

Briefly, in accordance with the present invention treatment of MS patients is carried out in two phases. First, an intense induction phase in which lymphocytapheresis is performed 3 to 5 times per week during which lymphocytes are removed continuously from the blood until the peripheral blood lymphocyte (PBL) count is less than 500 cells/$\mu$l as tested on three consecutive days. Second, in a maintenance phase patients are treated with LCP about once every 3 weeks for 6 months and then once every 4 weeks indefinitely, or as required to reduce the PBL count to less than about 500 cells/$\mu$l and preferably less than 300 cells/$\mu$l. After the induction phase as soon as the PBL count is depleted to the level of about 500 cells/$\mu$l, chemotherapy is started with an immunosuppresive or immunomodulating agent such as azathioprine, 2.5 mg/Kg. The addition of prednisone to this combined $R_x$ is preferred. Therapy is continued with both lymphocytaphersis and chemo-immunotherapy to maintain the PBL count at less than about 500 cells/$\mu$l and preferably less than 300 cells/$\mu$l.

The invention will be better understood by reference to the following detailed description and figures.

THE FIGURES

FIG. 1 is a bar chart illustrating the clinical results achieved with the invention, and FIG. 2 is a bar chart similar to FIG. 1 illustrating results achieved in a prior art method.

DETAILED DESCRIPTION OF THE INVENTION

Figure 1:
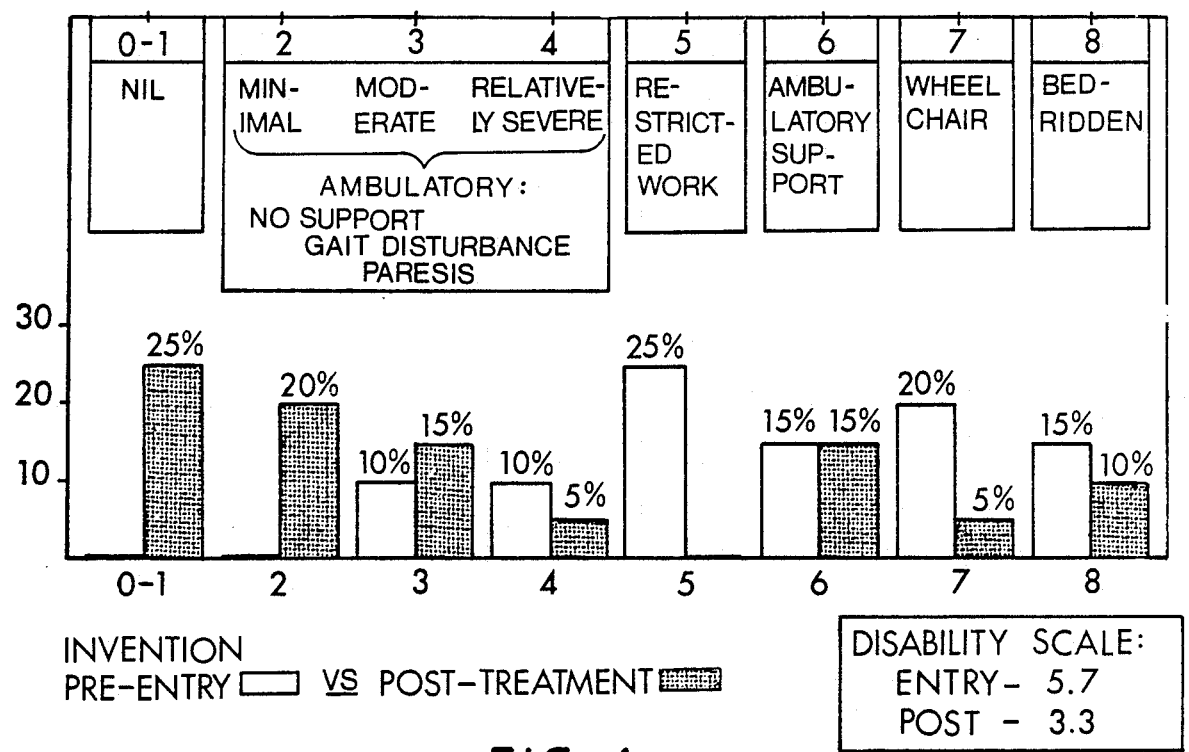

While the pathogenesis of MS is unknown, the pathologic process results in demyelination of the nerve axons in the central nervous system accompanied by inflammation and gliosis. Recent evidence indicates, as pointed out above, that MS is an autoimmune disease that appears to involve a defective immune response. The exact role of the T8 and T4 cells is unknown, but the peripheral blood lymphocytes (PBL) are believed by me to be in equilibrium with those in the brain so that there is a continuous recruitment of blood lymphocytes from the blood into the brain. It is to be noted that the MS plaques are most often found adjacent to the periventricular blood vessels of the brain.

The approach of the present invention is to radically reduce the peripheral blood lymphocyte mass to a predetermined level as measured by the numbers of lymphocytes removed and especially the numbers of PBL remaining, and to maintain this level. After treatment the patient then becomes sufficiently immunologically unresponsive to control the disease. While the primary effect is believed to be the elimination of an inappropriate immune reaction, treatment may also remove lymphocytes activated against the central nervous system. Evidence indicates the existence of circulating lymphocytes which are directed presumably against the myelin substance. While in the past there has been evidence that autoimmunity is involved in plaque formation, previously none of the means for reducing the immune reaction have been as effective as the present method in maintaining immune suppression and protecting the patient from exacerbations. After treatment in accordance with the present method, the number of PBL are lowered to a predetermined level. Thereafter the recruitment of lymphocytes from the peripheral blood is strikingly reduced and there are therefore fewer cells available to infiltrate the central nervous system. The improved results obtained through the present invention are due in large part to achieving control over PBL depletion and in finding a way to maintain this control. It has now been found that from about 90 to $250 \times 10^9$ lymphocytes must be removed from a human patient for the treatment to be effective.

METHOD OF LYMPHOCYTE DEPLETION

In the process of lymphocytapheresis, lymphocytes are removed by any known lymphocytapheresis equipment. In the present work a Quinton double lumen catheter or a Scribner shunt are used during the induction phase. In the latter procedure, access is achieved by insertion of a U-tube into an artery and a vein of the wrist or forearm by a surgeon. The U-tube is then connected to the LCP centrifuge. In the maintenance phase, the Scribner shunt is converted to an arteriovenous fistula. Lymphocytapheresis is then performed using two needles inserted into the fistula. One serves to continuously withdraw blood and the other continuously returns the blood after lymphocytapheresis. To the fistula where the artery and vein are connected, two needles are attached, one to withdraw and one to return blood continuously to the patient.

Cell removal is accomplished using any suitable equipment. One preferred LCP apparatus is known as a CS 3000 by Fenwall Division of Baxter Laboratories, Round Lake, Ill. Alternatively, an IBM 2995 or a Haemoneters Model 30 or a PEX can be used.

The CS 3000 was operated at a speed of 1600 rpm, resulting in removal of 95% of the lymphocytes together with a small number of platelets and erythrocytes. The blood flow is set at 60 ml/min. The chamber employed is granulocyte A35 with platelet sparing insert.

INDUCTION PHASE TREATMENT

During the initial or induction phase, an intense lymphocytapheresis program is carried out. During each treatment, 5 to 6 liters of plasma are processed per treatment and continuously returned to the body. Treatment is continued until 5,000 cc of plasma have passed through the centrifuge, at which time treatment is terminated for the day. Treatment can be terminated earlier if dictated by patient fatigue. Five treatments are carried out in the first week; thereafter, three treatments are given per week until the following criteria are met: the patient has a PBL count of less than 500 lymphocytes/$\mu$l on three consecutive days of treatment and the number of lymphocytes removed per treatment is about 3 to $4 \times 10^9$.

The number of treatments required in the induction phase varies from about 15 to 25 depending upon the size and weight of the patient. In any event, the removal of a total of about 90 to $250 \times 10^9$ lymphocytes over a period of from about five to seven weeks is accomplished, resulting at the end of that time in a PBL count of less than about 500 lymphocytes/$\mu$l on three consecutive days of treatment. PBL count is done conventionally by microscopic examination or automated differential cell counter methods.

MAINTENANCE PHASE TREATMENT

In the maintenance phase, chemotherapy is instituted with an immunosuppressive or immunomodulating chemotherapeutic compound adapted to reduce the formation or activation of lymphocytes. One preferred regimen is azathioprine (AZA) administered at about 2.5 mg/Kg combined with prednisone at the dosage described below.

In addition to the chemotherapy, during the maintenance phase lymphocytapheresis is continued every three weeks for six months and then every four weeks indefinitely. During each LCP treatment the goal is to maintain a removal level per treatment of 1.5 to $2 \times 10^9$ lymphocytes and preferably less than $1.5 \times 10^9$ removed per treatment. The precise numbers removed will depend upon the efficiency of the cytapheresis machine employed. At the beginning of the induction phase total lymphocytes removed may be from about 10 to $25 \times 10^9$ lymphocytes per treatment. Later in the program, only about 1 to $2 \times 10^9$ lymphocytes are typically removed per treatment because of the lymphocyte depletion in the peripheral blood.

It is important to note that the chemotherapy is started only after the induction phase when the depleted state is reached as defined above. Chemotherapy is not started earlier because it is believed to be undesirable to stop the production of white blood cells prior to depletion. It has been found to be undesirable to start chemotherapy prior to the removal of the unaltered lymphocytes. Treatment dosage with AZA (e.g., Imuran ® by Burroughs Wellcome Drug Company) is graduated as follows: day 1, 5 mg/Kg; day 2, 4 mg/Kg; day 3, 4 mg/Kg; day 4 and thereafter, 2.5 mg/Kg per day. The AZA appears to function by slowing the production of lymphocytes. Prednisone, when used, is started at 60 mg/day orally and reduced daily by 5 mg/day decrements at weekly intervals to a maintenance dose of 15 mg/day. It is recommended that the prednisone be further reduced to 15 mg every second day one year after induction or after the most recent exacerbation.

Throughout the maintenance phase, the lymphocyte count is held to less than 500 cells/$\mu$l and preferably in most patients to a level of less than 300 cells/$\mu$l.

CLINICAL RESULTS

A total of 19 human patients were treated. All of these patients exhibited chronic progression of the disease prior to treatment as determined by the Kurtzke Disability Status Score indicated in FIG. 1. See: Rose, Kuzma, Kurtzke, Sibley and Tourtellotte, "Cooperative Study in the Evaluation of Therapy in Multiple Sclerosis: ACTH vs Placebo in Acute Exacerbations. Preliminary Report." *Neurology* (Minneapolis), 1968, 18 (6; Part 2).

The following overall results were achieved. Eighty percent were improved, 5% were stabilized and 15% progressed. A total of 3 patients ultimately dropped out within the first year. Two of them interrupted their course of treatment, one after 9 months and the other after 4 months. Three patients progressed in spite of treatment. In all three patients, the treatment was discontinued in their second year because of treatment failure. All the patients that responded to the combined therapy had chronic progressive disease for 2 to 14 years. At entry, 6 patients (35%) were working, while after treatment 12 (71%) were working. At entry, 11 were disabled and unable to work. Following treatment, 7 returned to work but 4 remained disabled.

Figure 2:
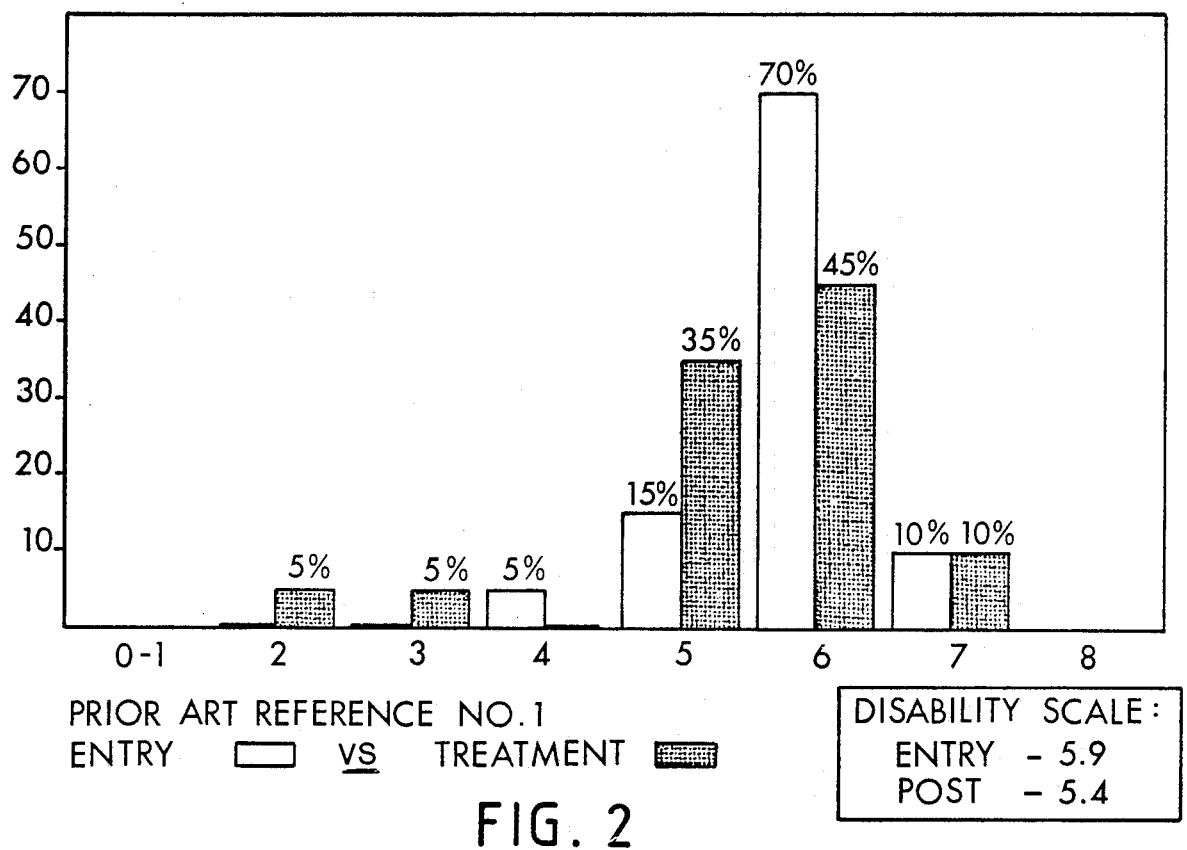

The effectiveness of the present method can be seen by reference to FIG. 1. Here a comparison can be made with the prior art treatment of reference 1 as shown in FIG. 2. It can be seen in FIG. 1 that prior to treatment with the present method there were no patients in Categories 1 and 2, but following treatment 45% of the patients entered these categories. Moreover, in the worst two categories (7 and 8) the numbers of patients were reduced from 20% to 5% and from 15% to 10%, respectively.

As shown in FIG. 1, the previous treatment described in reference 1 does not show the marked shift into the first three categories of the disability scale. The numbers of patients in Categories 1 and 2 increased by only 5% and there was no decrease in the numbers of patients in Categories 7 and 8.

In the present invention there were exacerbations in 17 instances. However, in 77% of these instances the patients responded to additional treatment.

Many variations are possible. For example, cyclosporin appears to be an effective adjunctive along with other chemotherapy and LCP. It appears that this drug may be required by only a few patients who are activating newly formed lymphocytes. Cyclosporin is preferably used only in treatment failures of the present protocol. The immunosuppressor or immunomodulating chemotherapeutic compounds make it possible to keep a patient in a cell-depleted state. Fewer new lymphocytes are being produced because the production of lymphocytes is reduced by the immunosuppressor. Another alternative immunosuppressive compound is 6-mercaptopurine administered at the dosage of 2.5 mg/Kg/day.

EXACERBATIONS

The present work indicates exacerbations and relapses are more likely to occur if lymphocyte counts are not kept at the limits established as outlined above. Forty-five percent of all the exacerbations were associated with high lymphocyte counts. In 3 patients who were unable to use AZA it was necessary to adjust the numbers of cytapheresis treatments. The numbers of treatments were increased to lower the lymphocyte count to the criteria levels established. In the treatment of patients having exacerbations, 3 to 9 booster treatments were used three times per week. If no response was obtained through this treatment, cyclosporin was administered to achieve a blood level between 50 to 150 mg/ml for 4 months or longer. Cyclosporin appears to arrest activation of new cells, while AZA slows down the proliferation of new lymphocytes so that fewer are being formed. Cyclosporin, on the other hand, may prevent existing cells from progressing from the resting to the activated state.

What is claimed is:

1. A method of treating demyelinating neuroimmunologic diseases in a human, comprising,
   removing blood from the patient,
   conducting lymphocytapheresis by separating and removing lymphocytes from the blood and returning the remaining fraction of the blood to the patient,
   conducting said lymphocytapheresis in a series of separate treatment steps, each treatment step comprising at least about 5000 cc of plasma, sufficient to reduce the peripheral blood lymphocyte count to less than about 500 cells/$\mu$l,
   administering an immunosuppressive or immunomodulating chemotherapeutic compound while continuing to administer said lymphocytapheresis steps at periodic intervals,
   said immunosuppressive or immunomodulating compound being administered in an amount sufficient together with the lymphocytapheresis treatments to remove over $90 \times 10^9$ lymphocytes and to maintain the peripheral blood lymphocyte count at less than about 500 cells/$\mu$l such that the human subject is immunologically unresponsive by an amount sufficient to control the disease.

2. The method of claim 1 wherein the immunosuppressive or immunomodulating chemotherapeutic compound comprises at least one member selected from the group consisting of prednisone, azathioprine, cyclophosphamide, cyclosporin and 6-mercaptopurine or a pharmacologically acceptable salt thereof.

3. The method of claim 2 wherein prednisone or a pharmacologically acceptable salt or precursor thereof is also administered to a human patient in an amount from about 60 mg to about 15 mg per day.

4. The method of claim 1 wherein the peripheral blood lymphocyte count is maintained below a level of about 300 cells/$\mu$l and following initial lymphocyte depletion only about 1.5 to $2.0 \times 10^9$ lymphocytes are removed per treatment.

5. The method of claim 1 wherein the immunosuppresive compound comprises azathioprine or a pharmacologically acceptable salt thereof administered in the amount of about 5 mg/Kg to about 2.5 mg/Kg per day.

6. The method of claim 5 wherein prednisone or a pharmacologically acceptable salt thereof is administered in the amount of from about 15 mg to 60 mg per day.

7. The method of claim 1 wherein the immunosuppressive compound comprises cyclosporin administered in an amount adapted to achieve a serum level of between about 50 and 150 mg/ml.

8. A method of treating demyelinating neuroimmunologic diseases in a human, comprising,
   removing blood from the patient,
   conducting lymphocytapheresis by separating and removing lymphocytes from the blood and returning the remaining fraction of the blood to the patient,
   the removing, separating and returning steps being performed substantially continously and simultaneously with one another,
   conducting said lymphocytapheresis in a series of separate treatment steps sufficient to reduce the peripheral blood lymphocyte count to less than about 500 cells/$\mu$l,
   administering an immunosuppressive or immunomodulating chemotherapeutic compound while continuing to administer said lymphocytapheresis steps at periodic intervals,
   said immunosuppressive or immunomodulating compound being administered in an amount sufficient together with the lymphocytapheresis treatments to remove from about $90-250 \times 10^9$ lymphocytes and to maintain the peripheral blood lymphocyte count at less than about 500 cells/$\mu$l such that the human subject is immunologically unresponsive by an amount sufficient to control the disease.

* * * * *